(12) United States Patent
Unno et al.

(10) Patent No.: US 7,101,432 B2
(45) Date of Patent: Sep. 5, 2006

(54) PROCESS FOR PRODUCING CRYSTALLINE TAGATOSE

(75) Inventors: Takehiro Unno, Fuji (JP); Yoshimi Watanabe, Suntou-gun (JP); Mikio Yamamoto, Fuji (JP)

(73) Assignee: Nihon Shokuhin Kako Co., Ltd., Tokyo (JP)

( * ) Notice: Subject to any disclaimer, the term of this patent is extended or adjusted under 35 U.S.C. 154(b) by 542 days.

(21) Appl. No.: 10/344,151

(22) PCT Filed: Aug. 7, 2001

(86) PCT No.: PCT/JP01/06789

§ 371 (c)(1),
(2), (4) Date: Feb. 10, 2003

(87) PCT Pub. No.: WO02/12257

PCT Pub. Date: Feb. 14, 2002

(65) Prior Publication Data

US 2005/0188912 A1    Sep. 1, 2005

(30) Foreign Application Priority Data

Aug. 8, 2000    (JP) .............................. 2000-239793

(51) Int. Cl.
C30B 7/08    (2006.01)
(52) U.S. Cl. .............................. 117/68; 117/69; 117/70
(58) Field of Classification Search .................. 117/68, 117/69, 70
See application file for complete search history.

(56) References Cited

U.S. PATENT DOCUMENTS

| | | | | |
|---|---|---|---|---|
| 5,002,612 A | * | 3/1991 | Beadle et al. | 127/46.1 |
| 5,078,796 A | * | 1/1992 | Beadle et al. | 127/46.1 |
| 6,057,135 A | * | 5/2000 | Ibrahim et al. | 435/105 |
| 2003/0022844 A1 | * | 1/2003 | Bertelsen et al. | 514/23 |

FOREIGN PATENT DOCUMENTS

| | | | |
|---|---|---|---|
| DE | 41 11 971 | | 3/1992 |
| EP | 532173 | | 3/1993 |
| EP | 609801 | | 8/1994 |
| EP | 0 709 463 | | 5/1996 |
| EP | 518874 | * | 5/1996 |
| JP | 5-504256 | | 7/1993 |
| JP | 5-308984 | | 11/1993 |
| JP | 6-145186 | | 5/1994 |
| JP | 8-92273 | | 9/1996 |
| WO | 92/12263 | | 7/1992 |

* cited by examiner

*Primary Examiner*—Robert Kunemund
(74) *Attorney, Agent, or Firm*—Oblon, Spivak, McClelland, Maier & Neustadt, P.C.

(57) ABSTRACT

The present invention provides a method for producing tagatose crystals from an aqueous system using no organic solvent. In this method, seed crystals of tagatose are added to a tagatose solution in which a tagatose purity of solid contents in the solution is at least 70% and a solid contents concentration in the solution is 60 to 98 mass %, and crystallization of tagatose is carried out by stirring and cooling the solution while keeping a degree of super saturation of tagatose at 1.25 or lower. It is preferred that the solution containing tagatose is a solution containing no organic solvent. It is further preferred that a part of massecuite for which the crystallization is completed is added to a mother liquor so as to produce the tagatose crystals semi-continuously or continuously. It is furthermore preferred that the tagatose crystals formed from the massecuite are separated by centrifugation or filtration and dried to obtain tagatose crystals.

19 Claims, No Drawings

PROCESS FOR PRODUCING CRYSTALLINE TAGATOSE

TECHNICAL FIELD

The present invention relates to a method for producing tagatose crystals from a tagatose solution containing no organic solvent.

BACKGROUND ART

Tagatose is a carbohydrate obtainable by isomerization of galactose. However, its existing content in nature is very low, and its characteristics are seldom known other than a few properties such as degree of sweetness, quality of taste and energy amount. The degree of sweetness of tagatose is about 90% of sugar, and its quality of taste is similar to fructose, and tagatose provides very fresh and sharp sweetness. Further, its energy amount is assumed to be 1.5 kcal/g, and it can be used as a low calorie sweetener.

As a method for producing tagatose crystals, a method wherein an organic solvent such as ethanol is added to a high purity tagatose solution for crystallization has been known. For example, Japanese International Publication No. 5-504256 discloses a method for obtaining tagatose crystals by adding seeds of tagatose crystals to a tagatose-containing syrup which contains ethanol.

However, since detailed characteristics of tagatose e.g. solubility of tagatose in water have not been known, there has been no report about a method for crystallization of tagatose from an aqueous system using no organic solvent.

DISCLOSURE OF INVENTION

Accordingly, it is an object of the present invention to provide a method for obtaining tagatose crystals from an aqueous system using no organic solvent.

The present inventors have conducted extensive studies on physical properties of tagatose, and as a result, found that tagatose crystals can be precipitated in a large amount by adding seed crystals to a high concentration aqueous solution. The present inventors have accomplished the present invention based on this discovery.

Namely, the method for producing tagatose crystals of the present invention is characterized by adding seed crystals of tagatose to a tagatose solution in which a tagatose purity of solid contents in the solution is at least 70% and a solid contents concentration in the solution is 60 to 98 mass %, and crystallizing tagatose by stirring and cooling the solution while keeping a degree of super saturation of tagatose at 1.25 or lower.

In the present invention, it is preferred that the solution containing tagatose is a solution containing no organic solvent. Further, it is preferred that a part of massecuite for which the crystallization is completed is added to a mother liquor so as to produce the tagatose crystals semi-continuously or continuously. Furthermore, it is preferred that the tagatose crystals formed from the massecuite are separated by centrifugation or filtration and dried to obtain tagatose crystals.

According to the present invention, it is possible to obtain tagatose crystals without using organic solvent, by adding seed crystals of tagatose to a tagatose solution in which a tagatose purity of solid contents in the solution is at least 70% and a solid contents concentration in the solution is 60 to 98 mass %, and crystallizing tagatose by stirring and cooling the solution while keeping a degree of super saturation of tagatose at 1.25 or lower.

BEST MODE FOR CARRYING OUT THE INVENTION

As the solution containing tagatose to be used in the present invention, a tagatose solution in which a tagatose purity of solid contents in the solution is at least 70% and a solid contents concentration in the solution is 60 to 98 mass % (hereinafter simply referred to as tagatose solution), is used. In the present invention, preferred is a tagatose solution in which a tagatose purity of solid contents in the solution is at least 90% and a solid contents concentration in the solution is 65 to 95 mass %. If the tagatose content in solid contents is less than 70%, tagatose crystals can not be precipitated. Further, if the solid contents concentration is less than 60 mass %, it is required to control the solution temperature at 20° C. or lower to form a saturated solution, whereby the energy costs are increased, such being not efficient. Moreover, if the solid contents concentration exceeds 98 mass %, the viscosity of the solution becomes too high, whereby the operation efficiency lowers and mimetic crystals are easily precipitated.

The tagatose solution can be obtained by known methods, and its preparation method is not particularly restricted. For example, the tagatose solution can be prepared by a method wherein galactose is isomerized by using a soluble alkali metal salt or alkaline earth salt to produce tagatose (Japanese International Publication No. 5-504256), a method wherein galactose is enzymatically isomerized by using L-arabinose or isomerase to obtain tagatose (U.S. Pat. No. 6,057,135), etc.

Further, the tagatose solution is preferably the one deionized with ion exchange resins, but may contain salts or colorants within a range not affecting the crystallization of tagatose.

Hereinafter, the method for producing tagatose crystals of the present invention will be described sequentially in order of steps.

1) Crystallization Operation

The above-mentioned tagatose solution is put in a container, and the solution temperature is maintained at a range of 30 to 80° C. Then, seed crystals of 0.006 to 80 mass % (tagatose crystals e.g. massecuite mentioned below) is added, and while stirring the solution, the solution temperature is lowered at a rate of 0.1 to 10° C./hour until the solution temperature reaches a range of 0 to 50° C., whereby tagatose crystals are precipitated. In the present invention, it is necessary to maintain the degree of supersaturation at 1.25 or lower during the crystallization operation, and for this purpose, it is important to conduct the above-mentioned accurate temperature control. When the degree of supersaturation is at 1.25 or lower, no particular problem will be caused in the production of crystals. However, if the degree of supersaturation exceeds this range, mimetic crystals tend to form, whereby separation of crystals will be very difficult. In the present invention, it is more preferred to maintain the degree of supersaturation at 1.05 or lower in order to precipitate the crystals uniformly in a large size. Here, the degree of supersaturation during the crystallization operation can be determined by sampling the massecuite, carrying out centrifugation at the temperature of the massecuite, and measuring the tagatose concentration of the supernatant.

2) Operation for Separating Crystals

Tagatose crystals can be separated by subjecting the solution (massecuite) for which crystallization operation is completed to e.g. centrifugation or filtration. Further, it is preferred to further washing the separated tagatose crystals with a small amount of water, followed by drying. By such operation, tagatose crystals having a purity of at least 85% can be obtained.

In the present invention, the massecuite may be used as seed crystals. For example, to a fresh tagatose solution, massecuite is added in an amount of 5 to 80 mass % of the solution, and crystallization operation of the above step 1) is carried out, whereby production of tagatose crystals can be conducted semi-continuously or continuously.

The structure of a crystallizer when the production of tagatose crystals is conducted semi-continuously or continuously as mentioned above, is not particularly restricted. As the crystallizer, crystallizers useful for the production of glucose crystals or fructose crystals may be mentioned.

Hereinafter, the present invention will be described in detail with reference to examples. However, the present invention is by no means restricted to these examples.

TEST EXAMPLE (MEASUREMENT OF SOLUBILITY OF TAGATOSE)

To 10 ml of deionized water at 10° C., 2 g of tagatose crystals (manufactured by Sigma Aldrich Japan Co.) was added one by one, and at the time when the tagatose crystals could no longer be dissolved, the temperature was gradually raised, and the temperature when the undissolved crystals were completely dissolved was read. Then, further 2 g of tagatose crystals was added, and same operation was repeated until the temperature reached around 70° C. The results are indicated in Table 1.

TABLE 1

| Tagatose concentration (mass %) | Dissolving temperature (° C.) |
|---|---|
| 58.3 | 20.0 |
| 61.5 | 29.6 |
| 64.3 | 37.5 |
| 66.7 | 45.8 |
| 68.8 | 57.5 |
| 70.6 | 68.9 |

From Table 1, the solubility curve of tagatose to water is obtained, and from the ratio of the concentration of tagatose solution at temperature (A)/the solubility of tagatose at temperature (A), the degree of supersaturation is obtained.

EXAMPLE 1

In accordance with the method in Example 1 described in Japanese International Publication No. 5-504256, steps from the isomerization to the treatment with ion exchange resins were carried out.

Isomerization 2,500 g of galactose (manufactured by Wako Junyaku Kogyo K.K.) was dissolved in 22,500 g of deionized water, and while stirring the solution at 20° C. (liquid temperature), 3,125 g of a slurry of calcium hydroxide (one obtained by dissolving 781 g of calcium hydroxide in 2,344 g of deionized water) was gradually added, to conduct isomerization. The progress of the reaction was checked by a HPLC analysis every 30minutes. After 5 hours, at which the conversion of galactose reached 80% or higher, phosphoric acid was gradually added to adjust pH of the reaction solution to 5.8, to terminate the reaction.

Treatment with Ion Exchange Resins

By subjecting the reaction solution to centrifugation, the filtrate and deposit were separately recovered. The deposit was washed with deionized water and then subjected to centrifugation again, and the recovered solid contents were mixed with the above filtrate. This mixed solution was allowed to pass through ion exchange resins (manufactured by Organo Corporation) for deionization treatment, and then concentrated, to obtain 2082.5 g of a tagatose solution having a tagatose purity of 82% and a solid contents concentration of 86 mass %.

341.8 g of the tagatose solution was put in a separable flask having an internal volume of 1,000 ml, and the solution temperature was adjusted to 68° C. while stirring in a water bath at 70° C. 0.03 g of seed crystals of tagatose crystals was added to this solution, and the temperature of the water bath was lowered at a rate of 2.5° C./hour, and at the time when the solution temperature reached 20° C., the solution was kept at this temperature for 5 hours.

The solution in the separable flask was used as massecuite containing crystals of tagatose and the solid content concentration in the solution portion in the massecuite was 78.7 mass %. The massecuite was subjected to centrifugation, and the resulting crystals were washed with a small amount of water, followed by drying, to obtain 211.3 g of tagatose crystals having a purity of 92%.

EXAMPLE 2

340.5 g of the tagatose solution obtained in Example 1 was put in a separable flask, and the same crystallization operation as in Example 1 was carried out. After completion of the crystallization operation, 50 g of massecuite was left in the separable flask, and 210.2 g of the tagatose solution obtained in Example 1 was added, and stirring was carried out for 15 minutes in a water bath of 70° C., and then the temperature of the water bath was lowered at a rate of 2.5° C./hour, and at the time when the solution temperature reached 20° C., the solution was kept at this temperature for 5 hours.

The obtained massecuite was subjected to centrifugation, and the resulting crystals were washed with a small amount of water, to obtain 205.8 g of tagatose crystals having a purity of 91%.

EXAMPLE 3

360.5 g of the tagatose solution obtained in Example 1 was put in a separable flask having an internal volume of 1,000 ml, and the solution temperature was adjusted to 68° C. while stirring in a water bath of 70° C. 0.02 g of seed crystals of tagatose crystals was added to this solution, and the temperature of the water bath was lowered at rates of 0.5° C./hour for the initial 5 hours, and subsequently, 1° C./hour for 5 hours, 1.5° C./hour for 5 hours, 2° C./hour for 5 hours and 2.5° C./hour for 10 hours, and at the time when the solution temperature reached 20° C., the solution was kept at this temperature for 5 hours.

The solution in the separable flask was used as massecuite containing crystals of tagatose, and this massecuite was subjected to centrifugation, and the resulting crystals were washed with a small amount of water, followed by drying, to obtain 195.6 g of tagatose crystals having a purity of 95%.

Comparative Example

The filtrate separated by centrifugation in Example 3 had a tagatose purity of 56%. This solution was concentrated to a solid content concentration of 84.8%, and the same crystallization as in Example 3 was attempted. However, the added seed crystals were dissolved and no precipitation of crystals was seen.

INDUSTRIAL APPLICABILITY

As explained above, according to the present invention, tagatose crystals can be obtained without using an organic solvent, by adding seed crystals of tagatose to a tagatose solution in which a tagatose purity of solid contents in the solution is at least 70% and a solid contents concentration in the solution is 60 to 98 mass %, and crystallizing tagatose by stirring and cooling the solution while keeping a degree of super saturation of tagatose at 1.25 or lower.

The invention claimed is:

1. A method for producing tagatose crystals, characterized by adding seed crystals of tagatose to a tagatose solution in which a tagatose purity of solid contents in the solution is at least 70% and a solid contents concentration in the solution is 60 to 98 mass %, and crystallizing tagatose by stirring and cooling the solution while keeping a degree of super saturation of tagatose at 1.25 or lower,
   wherein the solution containing tagatose is a solution containing no organic solvent.

2. The method for producing tagatose crystals according to claim 1, wherein a part of massecuite for which the crystallization is completed is added to a mother liquor so as to produce the tagatose crystals semi-continuously or continuously.

3. The method for producing tagatose crystals according to claim 1, wherein tagatose crystals formed from the massecuite are separated from centrifugation or filtration and dried to obtain tagatose crystals.

4. The method for producing tagatose crystals according to claim 3, wherein a part of massecuite for which the crystallization is completed is added to a mother liquor so as to produce the tagatose crystals semi-continuously or continuously.

5. The method for producing tagatose crystals according to claim 4, wherein tagatose crystals formed from the massecuite are separated from centrifugation or filtration and dried to obtain tagatose crystals.

6. A method for producing tagatose crystals, characterized by adding seed crystals of tagatose to a tagatose solution in which a tagatose purity of solid contents in the solution is at least 70% and a solid contents concentration in the solution is 60 to 98 mass %, and crystallizing tagatose by stirring and cooling the solution while keeping a degree of super saturation of tagatose at 1.25 or lower,
   wherein a part of massecuite for which the crystallization is completed is added to a mother liquor so as to produce the tagatose crystals semi-continuously or continuously.

7. The method for producing tagatose crystals according to claim 6, wherein the solution containing tagatose is a solution containing no organic solvent.

8. The method for producing tagatose crystals according to claim 6, wherein tagatose crystals formed from the massecuite are separated from centrifugation or filtration and dried to obtain tagatose crystals.

9. A method for producing tagatose crystals, characterized by adding seed crystals of tagatose to a tagatose solution in which a tagatose purity of solid contents in the solution is at least 70% and a solid contents concentration in the solution is 60 to 98 mass %, and crystallizing tagatose by stirring and cooling the solution while keeping a degree of super saturation of tagatose at 1.25 or lower,
   wherein tagatose crystals formed from the massecuite are separated from centrifugation or filtration and dried to obtain tagatose crystals.

10. The method for producing tagatose crystals according to claim 9, wherein the solution containing tagatose is a solution containing no organic solvent.

11. The method for producing tagatose crystals according to claim 9, wherein a part of massecuite for which the crystallization is completed is added to a mother liquor so as to produce the tagatose crystals semi-continuously or continuously.

12. The method for producing tagatose crystals according to claim 10, wherein a part of massecuite for which the crystallization is completed is added to a mother liquor so as to produce the tagatose crystals semi-continuously or continuously.

13. The method for producing tagatose crystals according to claim 12, wherein tagatose crystals formed from the massecuite are separated from centrifugation or filtration and dried to obtain tagatose crystals.

14. A method for producing tagatose crystals, characterized by adding seed crystals of tagatose to a tagatose solution in which a tagatose purity of solid contents in the solution is at least 70% and a solid contents concentration in the solution is 60 to 98 mass %, and crystallizing tagatose by stirring and cooling the solution while keeping a degree of super saturation of tagatose at 1.25 or lower,
   wherein the solution containing tagatose is a solution containing no organic solvent, and
   wherein a part of massecuite for which the crystallization is completed is added to a mother liquor so as to produce the tagatose crystals semi-continuously or continuously.

15. The method for producing tagatose crystals according to claim 14, wherein tagatose crystals formed from the massecuite are separated from centrifugation or filtration and dried to obtain tagatose crystals.

16. A method for producing tagatose crystals, characterized by adding seed crystals of tagatose to a tagatose solution in which a tagatose purity of solid contents in the solution is at least 70% and a solid contents concentration in the solution is 60 to 98 mass %, and crystallizing tagatose by stirring and cooling the solution while keeping a degree of super saturation of tagatose at 1.25 or lower,
   wherein tagatose crystals formed from a massecuite are separated from centrifugation or filtration and dried to obtain tagatose crystals.

17. The method for producing tagatose crystals according to claim 16, wherein the solution containing tagatose is a solution containing no organic solvent.

18. The method for producing tagatose crystals according to claim 16, wherein a part of massecuite for which the crystallization is completed is added to a mother liquor so as to produce the tagatose crystals semi-continuously or continuously.

19. The method for producing tagatose crystals according to claim 16, wherein tagatose crystals formed from the massecuite are separated from centrifugation or filtration and dried to obtain tagatose crystals.

* * * * *